US011445674B2

(12) United States Patent
Poland et al.

(10) Patent No.: US 11,445,674 B2
(45) Date of Patent: *Sep. 20, 2022

(54) WHEAT LINES, PLANTS, AND GRAIN WITH INCREASED BETA-GLUCAN CONTENT (71) Applicants: General Mills, Inc., Minneapolis, MN (US); Kansas State University Research Foundation, Manhattan, KS (US)

(72) Inventors: Jesse Poland, Junction City, KS (US); Bernd Friebe, Manhattan, KS (US); Titiana Danilova, Manhattan, KS (US); Bikram S Gill, Manhattan, KS (US); Eric Jackson, Wamego, KS (US)

(73) Assignees: General Mills, Inc., Minneapolis, MN (US); Kansas State University Research Foundation, Manhattan, KS (US)

( * ) Notice: Subject to any disclaimer, the term of this patent is extended or adjusted under 35 U.S.C. 154(b) by 120 days.

This patent is subject to a terminal disclaimer.

(21) Appl. No.: 17/037,828

(22) Filed: Sep. 30, 2020

(65) Prior Publication Data
US 2021/0015063 A1 Jan. 21, 2021

Related U.S. Application Data (63) Continuation of application No. 16/534,532, filed on Aug. 7, 2019, now Pat. No. 10,827,702, which is a continuation of application No. 16/484,224, filed as application No. PCT/US2018/018027 on Feb. 13, 2018, now abandoned.

(60) Provisional application No. 62/458,076, filed on Feb. 13, 2017.

(51) Int. Cl.
*A01H 5/10* (2018.01)
*A01H 6/46* (2018.01)

(52) U.S. Cl.
CPC ............. *A01H 6/4678* (2018.05); *A01H 5/10* (2013.01)

(58) Field of Classification Search
None
See application file for complete search history.

(56) References Cited

U.S. PATENT DOCUMENTS

| 9,603,329 | B2 * | 3/2017 | Johnson | A01H 6/4678 |
| 10,827,702 | B2 * | 11/2020 | Poland | A01H 6/4678 |
| 2009/0169683 | A1 | 7/2009 | Findlay | |
| 2012/0227126 | A1 | 9/2012 | Dolan | |
| 2015/0289466 | A1 | 10/2015 | Hu | |
| 2016/0251670 | A1 | 9/2016 | Jobling et al. | |

OTHER PUBLICATIONS

Cseh et al, 2013, Ann. Appl. Biol., 163:142-150.*
Türkösi et al., "Addition of Manas Barley Chromosome Arms to the Hexapioid Wheat Genome", BMC Genetics, vol. 17, No. 1, pp. 1-13, 2016.
Altschul et al., "Basic Local Alignment Search Tool", Journal of Molecular Biology, No. 215, pp. 403-410, 1990.
Danilova et al., "Single-Copy Gene Fluorescence in situ Hybridization and Genome Analysis: Acc-2 Loci Mark Evolutionary Chromosomal Rearrangements in Wheat", Chromosoma, No. 121, pp. 597-611, 2012.
Danilova et al., "Development of a Wheat Single Gene FISH Map for Analyzing Homoeologous Relationship and Chromosomal Rearrangements within the Triticeae", Theoretical and Applied Genetics, No. 127, pp. 715-730, 2014.
Islam et al., "Production and Characterization of Wheat-Barley Addition Lines", Proceedings of the Fifth International Wheat Genetics Symposium, New Delhi, pp. 365-371, 1978.
Islam et al., "Isolation and Characterization of Euplasmic Wheat-Barley Chromosome Addition Lines", Heredity, vol. 46, No. 2, pp. 161-174, 1981.
Hu et al., "Modification of Standard Enzymatic Protocol to a Cost-Efficient Formatfor Mixed-Linkage $(1\rightarrow 3,1\rightarrow 4)$-β-D-Glucan Measurement", Cereal Chemistry, No. 85, pp. 648-653, 2008.
Kato et al., "Sensitive Fluorescence in situ Hybridization Signal Detection in Maize Using Directly Labeled Probes Produced by High Concentration DNA Polymerase Nick Translation", Biotechnic & Histochemistry, No. 81, pp. 71-78, 2006.
Kato et al., "Chromosome Painting Using Repetitive DNA Sequences as Probes for Somatic Chromosome Identification in Maize", Proceedings of the National Academy of Sciences of the United States of America, vol. 101, No. 37, pp. 13554-13559, 2004.
Manninen et al., Bare-1, a Copia-Like Retroelement in Barley (Hordeum Vulgare L.), Plant Molecular Biology, No. 22, pp. 829-846, 1993.
Mayer et al., "A Chromosome-Based Draft Sequence of the Hexapioid Bread Wheat (Triticum Aestivum) Genome", Science, vol. 345, pp. 286-300, 2014.
Mayer et al., "A Physical, Genetic and Functional Sequence Assembly of the Barley Genome", Nature, vol. 491, pp. 711-717, 2012.
Waugh et al., "Genetic Distribution of Bare-1-Like Retrotransposable Elements in the Barley Genome Revealed by Sequence-Specific Amplification Polymorphisms (S-SAP)", Molecular & General Genetics, No. 253, pp. 687-694, 1997.
Wicker et al., "A Whole-Genome Snapshot of 454 Sequences Exposes the Composition of the Barley Genome and Provides Evidence for Parallel Evolution of Genome Size in Wheat and Barley", Plant Journal, No. 59, pp. 712-722, 2009.
Zhang et al., "The Centromere Structure in Robertsonian Wheat-Rye Translocation Chromosomes Indicates that Centric Breakage-Fusion Can Occur at Different Positions within the Primary Constriction", Chromosoma, No. 110, pp. 335-344, 2001.

(Continued)

Primary Examiner — Jason Deveau Rosen
(74) Attorney, Agent, or Firm — Diederiks & Whitelaw, PLC; Annette M. Fraawley, Esq.

(57) ABSTRACT

The present disclosure relates to wheat plants having grain with high β-glucan content, methods for constructing said wheat plants, grain therefrom and uses thereof. Wheat lines homozygous for the HvCslF6 gene from barley having five times the fiber content and an increased β-glucan content of TA5790, TA5792, and TA5795 are disclosed.

8 Claims, 4 Drawing Sheets
Specification includes a Sequence Listing.

(56) References Cited

OTHER PUBLICATIONS

Molnar-Lang et al., *Detection of Wheat-Barley Translocations by Genomic in situ Hybridization in Derivatives of Hybrids Multiplied in Vitro*, Euphytica, vol. 112, pp. 117-123, 2000.

Cseh et al., "*Expression of HcCsIF9 and HvCsIF6 Barley Genes in the Genetic Background of Wheat and Their Influence on the Wheat β-Glucan*", Annals of Applied Biology, No. 163, pp. 142-150, 2013.

* cited by examiner

SEQUENCE LISTING

```
<160> NUMBER OF SEQ ID NOS: 10

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgcagaacta gcacaagtat ccatag                                           26

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgcagaacta gcacaagtat ccact                                            25
```

```
<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcagattcta agagtattgg attctgga                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcagattcta agagtattgg cttccggg                                          28

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggagtgacg aatgggtt                                                     18

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccmctgcgc aggataagag a                                                 21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatgtgggga gttgatgatg ac                                                22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctggaagct gaatcgaatt tac                                               23
```

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agcaagagag acggaaaggt aga                                           23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgatctagtg ccgaacggac gac                                           23
```

WHEAT LINES, PLANTS, AND GRAIN WITH INCREASED BETA-GLUCAN CONTENT

CROSS-REFERENCE TO RELATED APPLICATIONS

This application represents a continuation of application Ser. No. 16/534,532 entitled "Wheat Lines, Plants, and Grain with Increased Beta-Glucan Content" filed Aug. 7, 2019, which is a continuation of application Ser. No. 16/484,224 entitled "Wheat Lines, Plants, and Grain with Increased Beta-Glucan Content" filed Aug. 7, 2019, which represents a National Stage application of PCT/US2018/018027 entitled "Wheat Lines, Plants, and Grain with Increased Beta-Glucan Content" filed Feb. 13, 2018, which claims the benefit of U.S. Provisional Application Ser. No. 62/458,076 entitled "Wheat Lines, Plants, and Grain with Increased Beta-Glucan Content. The entire content of these applications is incorporated herein by reference.

SEQUENCE LISTING

The instant application contains a Sequence Listing which has been submitted electronically in ASCII format and is hereby incorporated by reference in its entirety. Said ASCII copy, created on Sep. 21, 2020, is named 7823U504_SL.txt and is 2,690 bytes in size.

FIELD OF THE INVENTION

The present invention relates to wheat with high levels of β-glucan, developed through traditional plant crossing and selection techniques and the use of this wheat. Methods of developing cultivars and varieties, specific lines, uses thereof as well as products derived therefrom are also disclosed.

BACKGROUND OF THE INVENTION

The cell wall polysaccharides of cereal grains are an important dietary component in human nutrition, as a source of dietary fiber. Cell wall polysaccharides constitute about 10% by dry weight of cereal grains and consumption of whole grain cereals is associated with a reduced risk of developing type 2 diabetes, cardiovascular disease and colorectal cancer. Consumption of whole grains also provides improved gastrointestinal health. Whole grains also have a relatively low glycemic index and are a rich source of other dietary components including vitamins, antioxidants and minerals, as well as starch as an energy source.

Cell wall polysaccharides include predominately β-1,4-glucan along with other polysaccharides such as arabino-(1,4)-β-D-xylan. The structure of β-glucan is unique among cell wall polymers in that it consists of a linear polymer of glucose residues linked covalently by 1-3 and 1-4 linkages, arranged in a non-repeating but non random fashion. The polysaccharide from barley grain also has approximately 10% longer β-1-4 linked cellodextrin units. The conformational asymmetry of the molecule enables the polymer to form a viscous porous gel like structure in the matrix of the plant cell wall.

Ingestion of β-glucan increases bile acid excretion leading to a reduction in total serum cholesterol and low density lipoproteins (LDL) with a lowering of the risk of coronary disease. Similarly, β-glucans act by attenuating excursions in postprandial blood glucose concentration. It is thought that both of these effects are based on the increase of viscosity in the contents of the stomach and intestines. β-glucans can be partially digested by endogenous colonic bacteria which gives rise to short chain fatty acids (predominantly acetate, propionate and butyrate) which are beneficial to mucosal cells lining the intestine and colon).

The β-glucan content of grains varies considerably amongst cereals, with barley, oats and rye having the highest amounts and wheat, maize and rice having relatively low levels. β-glucan content of wild-type whole wheat grain is about 0.6% on a weight basis, compared to about 4.2% for barley, 3.9% for oats and 2.5% for rye. In wheat endosperm, cell walls comprise about 70% arabino-(1,4)-β-D-xylan and 15-25% β-glucan, along with about 4% cellulose ((1,4)-β-D-glucan) and about 7% (1,4)-β-D-glucomannans. In contrast, barley endosperm cell walls have about 20% arabino-(1,4)-β-D-xylan and 70% β-glucan. Rice grain cell walls also have significant levels of cellulose (20%). The reasons why wheat grain has relatively low β-glucan levels, much lower than barley or oats, and why wheat β-glucan has a different structure than other cereal (3-glucans are unknown.

There is considerable health and economic benefit to be derived from the increase of β-glucan content in cereal grains, particularly wheat, which is the most commonly consumed higher fiber content cereal grain.

SUMMARY OF THE INVENTION

One aspect of the present invention relates to wheat lines with increased β-glucan content that have been developed through crossing and traditional breeding and selection techniques of cereal plants. According to the invention wheat lines 2015-627-41, 75; 2015-630-15 and 2015-629-23 developed from crossing and selection with barley have been developed which have up to five times the soluble fiber found in traditional wheat plants, and 1.4 to 1.8 times higher β-glucan content than a control or traditional wheat plant. The plants are all homozygous for the barley cellulose-synthase-like CslF6 gene which was introgressed through traditional breeding from the Barley lines Betzes. In general, these cultivars have up to 2% of total grain weight as β-glucan.

The invention also includes seeds of these plants. The invention also relates to plants produced by growing the seed of the wheat plants of the invention, as well as the derivatives of such plants. Further provided are plant parts, including cells, plant protoplasts, plant cells of a tissue culture from which wheat plants can be regenerated, plant calli, plant clumps, and plant cells that are intact in plants or parts of plants, such as leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells, and the like.

Another aspect of the invention relates to a tissue culture of regenerable cells of the high β-glucan wheat plant, as well as plants regenerated therefrom. Yet another aspect of the current invention is a wheat plant developed from the wheat lines of the invention. Still yet another aspect of the invention relates to a first generation ($F_1$) hybrid wheat seed produced by crossing a plant of the high β-glucan wheat plants of the invention to a second wheat plant. Also included in the invention are the $F_1$ hybrid wheat plants grown from the hybrid seed produced by crossing the high β-glucan wheat cultivar with a second wheat plant. Still further included in the invention are the seeds of an $F_1$ hybrid plant produced with the high β-glucan wheat plant as one parent, the second generation ($F_2$) hybrid wheat plant grown from the seed of the $F_1$ hybrid plant, and the seeds of the $F_2$ hybrid plant.

Still yet another aspect of the invention is a method of producing wheat seeds comprising crossing a plant of the high β-glucan wheat cultivar to any second wheat plant, including itself or another plant of the β-glucan wheat cultivar of the invention. In particular embodiments of the invention, the method of crossing comprises the steps of: (a) planting seeds of a high β-glucan wheat plant; (b) cultivating wheat plants resulting from said seeds until said plants bear flowers; (c) allowing fertilization of the flowers of said plants; and (d) harvesting seeds produced from said plants.

Still yet another aspect of the invention is a method of producing hybrid wheat seeds comprising crossing the high β-glucan wheat plant to a second, distinct wheat plant that is nonisogenic to the high β-glucan wheat cultivar. In particular embodiments of the invention, the crossing comprises the steps of: (a) planting seeds of high β-glucan wheat cultivar and a second, distinct wheat plant, (b) cultivating the wheat plants grown from the seeds until the plants bear flowers; (c) cross pollinating a flower on one of the two plants with the pollen of the other plant, and (d) harvesting the seeds resulting from the cross pollinating.

Still yet another aspect of the invention is a method for developing a wheat plant in a wheat breeding program comprising: (a) obtaining a wheat plant, or its parts, of high β-glucan wheat cultivar; and (b) employing said plant or parts as a source of breeding material using plant breeding techniques. In the method, the plant breeding techniques may be selected from the group consisting of recurrent selection, mass selection, bulk selection, backcrossing, pedigree breeding, genetic marker-assisted selection and genetic transformation. In certain embodiments of the invention, the high β-glucan wheat cultivar may be used as the male or female parent.

Still yet another aspect of the invention is a method of producing a wheat plant derived from high β-glucan wheat cultivar, the method comprising the steps of: (a) preparing a progeny plant derived from high β-glucan wheat cultivar by crossing a plant of high β-glucan wheat cultivar with a second wheat plant; and (b) crossing the progeny plant with itself or a second plant to produce a progeny plant of a subsequent generation which is derived from a plant of the high β-glucan wheat cultivar. In one embodiment of the invention, the method further comprises: (c) crossing the progeny plant of a subsequent generation with itself or a second plant; and (d) repeating steps (b) and (c) for, in some embodiments, at least 2, 3, 4 or more additional generations to produce an inbred wheat plant derived from the high β-glucan wheat cultivar which retains the high β-glucan trait. Also provided by the invention is a plant produced by this and the other methods of the invention.

In another embodiment of the invention, the method of producing a wheat plant derived from a high β-glucan wheat cultivar further comprises: (a) crossing high β-glucan wheat cultivar-derived wheat plant with itself or another wheat plant to yield additional high β-glucan wheat cultivar-derived progeny wheat seed; (b) growing the progeny wheat seed of step (a) under plant growth conditions to yield additional high β-glucan-derived wheat plants; and (c) repeating the crossing and growing steps of (a) and (b) to generate further β-glucan-derived wheat plants. In specific embodiments, steps (a) and (b) may be repeated at least 1, 2, 3, 4, or 5 or more times as desired. The invention still further provides a wheat plant produced by this and the foregoing methods.

This invention also relates to processes for making a wheat plant containing in its genetic material one or more high β-glucan traits introgressed from a high β-glucan wheat variety through backcross conversion and/or transformation, and to the wheat seed, plant and plant parts produced thereby. This invention also relates to the creation of variants by mutagenesis or transformation of a high β-glucan wheat variety. This invention further relates to a hybrid wheat seed, plant or plant part produced by crossing the high β-glucan cultivar or a locus conversion of a high β-glucan cultivar with another wheat variety.

DESCRIPTION OF THE FIGURES

FIG. 1. FISH mapping. A. CslF6 loci were detected near the centromere on the long arms of all group 7 wheat chromosomes and barley. B. Physical mapping of molecular markers: barley cDNA AK353650 was detected on barley and wheat chromosomes. Chromosomes were identified by (GAA)n banding, note, e.g., chromosomes labeled 11-18. cDNAs are labeled, e.g., at 21-28, chromosomes counterstained with DAPI, are labeled, e.g., at 31-38. Average distance from centromere: CslF6: 7HL 0.13±0.03; 7AL 0.11±0.03; 7BL 0.04±0.02; 7DL 0.11±0.02; AK353650: 7HS 0.93±0.02; 7AS 0.94±0.02 4AL 0.96±0.01; 7DS 0.94±0.03.

FIG. 2. Genotyping with chromosome 7 KASP markers. The co-dominant KASP assays correctly identified plants homozygous on barley alleles (cv 'Betzes', circles), heterozygous (ditelosomic addition lines, TA3588, 7HS for marker 10 and TA3587, 7HL for marker 5 triangles), and homozygous on wheat alleles (cv CS, squares). Diamonds are blank samples (no call). Physical positions of the markers on group 7 chromosomes are shown on the left.

FIG. 3. Cytogenetic analysis of translocation chromosomes. A. Short arms of wheat group-7 chromosomes in translocation chromosomes T7WS•7HL were identified by FISH with cDNA probe 7S-4. FISH images are shown in the left, GISH images are in the right B. Long arms of wheat group-7 chromosomes in translocation T7HS•7WL were identified by their (GAA)n pattern (on the left). FISH: (GAA)n and pAs1 repeats are labeled, e.g., at 41-46; cDNA probe 7S-4 is shown, e.g., at 51-53; chromosomes counterstained with DAPI, are labeled, e.g., at 61-63. GISH: barley chromatin is labeled, e.g., at points 71-76; (GAA)n repeats are labeled, e.g., at 81-86; chromosomes counterstained with PI are labeled, e.g., at 91-96.

FIG. 4. Chromosomes of plants, homozygous on compensating RobTs. A, B, E, F—GISH: barley gDNAs is shown, e.g., at 101-104, (GAA)n—repeats are labeled, e.g., at 111-114, chromosomes counterstained in PI are labeled, e.g., at 121-124. C, D—FISH: BARE-repeat, hybridized to barley chromatin is labeled, e.g., at points 131, 132, pAs1-repeat is (GAA)n—repeat is shown at, e.g., points 141-142.

DETAILED DESCRIPTION OF THE INVENTION

Definitions

About: Refers to embodiments or values that include the standard deviation of the mean for a given item being measured.

Allele: Any of one or more alternative forms of a gene locus, all of which relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid (F$_1$), back to one of the parents of the hybrid progeny. Backcrossing can be used to introduce one or more single locus conversions, or one or more traits (such as high β-glucan content) from one genetic background into another.

As used herein, the term "barley" refers to any species of the Genus *Hordeum*, including progenitors thereof, as well as progeny thereof produced by crosses with other species. Examples of *Hordeum* species include but are not limited to: *Hordeum arizonicum* Covas—Arizona barley P; *Hordeum bogdanii* Wilensky P; *Hordeum brachyantherum* Nevski—meadow barley P (including Subspecies *Hordeum brachyantherum* Nevski ssp. *brachyantherum*—meadow barley P and *Hordeum brachyantherum* Nevski ssp. *californicum* (Covas & Stebbins) Bothmer, N. Jacobsen & Seberg—California barley P); *Hordeum brevisubulatum* (Trin.) Link P; *Hordeum bulbosum* L.—bulbous barley P; *Hordeum comosum* J. Presl P; *Hordeum depressum* (Scribn. & J. G. Sm.) Rydb.—dwarf barley P; *Hordeum intercedens* Nevski—bobtail barley P; *Hordeum jubatum* L.—foxtail barley P (including Subspecies *Hordeum jubatum* L. ssp. *intermedium* Bowden—intermediate barley P and *Hordeum jubatum* L. ssp. *jubatum*—foxtail barley P); *Hordeum marinum* Huds.—seaside barley P; (including subspecies *Hordeum marinum* Huds. ssp. *gussoneanum* (Parl.) Thell.—Mediterranean barley P and *Hordeum marinum* Huds. ssp. *marinum*—seaside barley P); *Hordeum murinum* L.—mouse barley P (including subspecies *Hordeum murinum* L. ssp. *glaucum* (Steud.) Tzvelev—smooth barley P, *Hordeum murinum* L. ssp. leporinum (Link) Arcang.—hare barley P, and *Hordeum murinum* L. ssp. *murinum*—wall barley P); *Hordeum parodii* Covas P; *Hordeum pusillum* Nutt.—little barley P; *Hordeum spontaneum* K. Koch—spontaneous barley P; and *Hordeum vulgare* L.—common barley P Also encompassed are plants that are produced by conventional techniques using *Hordeum* sp. as a parent in a sexual cross with a non-*Hordeum* species, such as rye *Secale cereale*, L., including but not limited to Triticale. Preferably the barley plant is suitable for commercial production of grain, such as commercial varieties of barley, having suitable agronomic characteristics which are known to those skilled in the art.

The term "β-glucan" as used herein, refers to non-starch polysaccharides of D-glucose monomers comprising B-(1, 4)-linked glucose units separated every 2-3 units by β-(1, 3)-linked glucose.

Cell: As used herein, the term cell includes a plant cell, whether isolated, in tissue culture, or incorporated in a plant or plant part.

Chromatography: A technique wherein a mixture of dissolved substances are bound to a solid support followed by passing a column of fluid across the solid support and varying the composition of the fluid. The components of the mixture are separated by selective elution.

Crossing: The mating of two parent plants.

Cross-pollination: Fertilization by the union of two gametes from different plants.

Disease Resistance: As used herein, the term disease resistance or disease resistant is defined as the ability of plants to restrict the activities of a specified disease, such as a fungus, virus, or bacterium.

Disease Tolerance: As used herein, the term disease tolerance or disease tolerant is defined as the ability of plants to endure a specified disease (such as a fungus, virus, or bacterium) or an adverse environmental condition and still perform and produce in spite of this disorder.

Emasculate: The removal of plant male sex organs or the inactivation of the organs with a cytoplasmic or nuclear genetic factor or a chemical agent conferring male sterility.

Embryo: The embryo is the small plant contained within a mature seed.

Enzymes: Molecules which can act as catalysts in biological reactions.

Essentially all of the morphological and physiological characteristics: The characteristics of a plant are recovered that are otherwise present when compared in the same environment, other than occasional variant traits that might arise during backcrossing or direct introduction of a transgene.

F$_1$ Hybrid: The first generation progeny of the cross of two nonisogenic plants.

Gene Converted (Conversion): Gene conversion or a gene converted plant refers to plants that are developed by backcrossing, genetic engineering, or mutation, wherein essentially all of the morphological and physiological characteristics of a variety are recovered, in addition to the one or more traits transferred into the variety via the backcrossing technique, genetic engineering, or mutation.

Gene Silencing: Gene silencing refers to the interruption or suppression of the expression of a gene at the level of transcription or translation.

Genotype: The genetic constitution of a cell or organism.

Grain: or any grammatically equivalent expression as used herein, refers to grain kernels from a wheat plant. In some exemplary embodiments, the term "grain" refers to grain kernels from a wheat plant having grain with high β-glucan content.

Haploid: A cell or organism having one set of the two sets of chromosomes in a diploid.

Herbicide Resistance: As used herein, the term herbicide resistance or herbicide resistant is defined as the ability of plants to survive and reproduce following exposure to a dose of herbicide that would normally be lethal to the plant.

Herbicide Tolerance: As used herein, the term herbicide tolerance or herbicide tolerant is defined as the ability of plants to survive and reproduce after herbicide treatment.

Insect Resistance: As used herein, the term disease resistance or disease resistant is defined as the ability of plants to restrict the activities of a specified insect or pest.

Insect Tolerance: As used herein, the term disease tolerance or disease tolerant is defined as the ability of plants to endure a specified insect or pest and still perform and produce in spite of this disorder.

Kernel Weight: As used herein, the term kernel weight refers to the weight of individual kernels (also called seeds), often reported as the weight of one thousand kernels or "1000 Kernel Weight."

Linkage: A phenomenon wherein alleles on the same chromosome tend to segregate together more often than expected by chance if their transmission was independent.

Locus: A locus is a position on a genomic sequence that is usually found by a point of reference, for example, the position of a DNA sequence that is a gene, or part of a gene or intergenic region. A locus confers one or more traits such as, for example, male sterility, herbicide tolerance or resistance, insect resistance or tolerance, disease resistance or tolerance, modified fatty acid metabolism, modified phytic acid metabolism, modified carbohydrate metabolism or modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Marker: A readily detectable phenotype, preferably inherited in codominant fashion (both alleles at a locus in a diploid heterozygote are readily detectable), with no environmental variance component, i.e., heritability of 1.

Or: As used herein is meant to mean "and/or" and be interchangeable therewith unless explicitly indicated to refer to the alternative only.

Pedigree Distance: Pedigree distance is the relationship among generations based on their ancestral links as evidenced in pedigrees. It may be measured by the distance of the pedigree from a given starting point in the ancestry.

Percent Identity: Percent identity, as used herein, refers to the comparison of the homozygous alleles of two wheat varieties. Percent identity is determined by comparing a statistically significant number of the homozygous alleles of two developed varieties. For example, a percent identity of 90% between wheat variety 1 and wheat variety 2 means that the two varieties have the same allele at 90% of their loci.

Phenotype: The detectable characteristics of a cell or organism, which characteristics are the manifestation of gene expression.

Plant: As used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to plants of any variety of ploidy levels, including polyploid, diploid, haploid and hemizygous.

Plant Parts: As used herein, the term plant parts (or reference to "a wheat plant, or a part thereof") includes, but is not limited to, protoplasts, callus, leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells.

Progeny: As used herein, progeny includes an F1 wheat plant produced from the cross of two wheat plants where at least one plant or an ancestor thereof includes a high β-glucan wheat plant of the invention.

Quantitative Trait Loci (QTL): Quantitative trait loci refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing and/or by genetic transformation to introduce a given locus that is transgenic in origin, wherein essentially all of the morphological and physiological characteristics of a wheat cultivar are recovered in addition to the characteristics of the locus transferred into the variety via the backcrossing technique or by genetic transformation. It is understood that once introduced into any wheat plant genome, a locus that is transgenic in origin (transgene), can be introduced by backcrossing as with any other locus.

Substantially Equivalent: A characteristic that, when compared, does not show a statistically significant difference (e.g., p=0.05) from the mean.

As used herein, the term "by weight" or "on a weight basis" refers to the weight of a substance, for example, β-glucan, as a percentage of the weight of the material or item comprising the substance. This is abbreviated herein as "w/w". Typically, the weight of β-glucan is determined as a percentage of the weight of the wheat wholemeal flour, assuming that wholemeal flour has a moisture content of 10%. This determination is according to the Megazyme kit for measuring β-glucan.

Tissue Culture: A composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, ovules, pericarp, flowers, florets, heads, spikelets, seeds, leaves, stems, roots, root tips, anthers, pistils, awns, stems, and the like.

Transgene: A genetic locus comprising a sequence which has been introduced into the genome of a wheat plant by transformation.

The terms "transgenic plant" and "transgenic wheat plant" as used herein refer to a plant that contains a gene construct ("transgene") not found in a wild-type plant of the same species, variety or cultivar introduced by recombinant DNA techniques. A "transgene" as referred to herein has the normal meaning in the art of biotechnology and refers to a genetic sequence which has been produced or altered by recombinant DNA or RNA technology and which has been introduced into a progenitor plant cell, which cell is used to produce a new plant. The transgene may include genetic sequences obtained from or derived from a plant cell, or another plant cell, or a non-plant source, or a synthetic sequence. Typically, the transgene has been introduced into the plant by human manipulation other than crossing such as, for example, by transformation but any method can be used as one of skill in the art recognizes. The genetic material is typically stably integrated into the genome of the plant. The introduced genetic material may comprise sequences that naturally occur in the same species but in a rearranged order or in a different arrangement of elements, for example an antisense sequence or a sequence encoding a double-stranded RNA or an artificial microRNA precursor. Plants containing such sequences are included herein in "transgenic plants". Transgenic plants as defined herein include all progeny of an initial transformed and regenerated plant (TO plant) which has been genetically modified using recombinant techniques, where the progeny comprise the transgene. Such progeny may be obtained by self-fertilization of the primary transgenic plant or by crossing such plants with another plant of the same species. In an embodiment, the transgenic plants are homozygous for each and every gene that has been introduced (transgene) so that their progeny do not segregate for the desired phenotype. Transgenic plant parts include all parts and cells of said plants which comprise the transgene such as, for example, seeds, cultured tissues, callus and protoplasts. A "non-transgenic plant", preferably a non-transgenic wheat plant, is one which has not been genetically modified by the introduction of genetic material by recombinant DNA techniques.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaeroocccum, T. vavilovii*, and interspecies cross thereof. Tetraploid wheat includes *T. durum* (also referred to as durum wheat or *Triticum turgidum* ssp. durum), *T. dicoccoides, T. dicoccum, T. polonicum*, and interspecies cross thereof. In addition, the term "wheat" includes possible progenitors of hexaploid or tetraploid *Triticum* sp. such as *T. uartu*, *T. monococcum* or *T. boeoticum* for the A genome, *Aegilops speltoides* for the B genome, and *T. tauschii* (also known as *Aegilops squarrosa* or *Aegilops tauschii*) for the D genome. A wheat plant or grain of the present invention may belong to, but is not limited to, any of the above-listed species. Also encompassed are plants that are produced by conventional techniques using *Triticum* sp. as a parent in a sexual cross with a non-*Triticum* species, such as rye *Secale cereale* L., including but not limited to Triticale. Preferably the wheat plant is suitable for commercial production of grain, such as commercial varieties of hexaploid wheat or durum wheat, having suitable agronomic characteristics which are known to those skilled in the art. More preferably the wheat is *Triticum aestivum* ssp. *aestivum* or *Triticum turgidum* ssp. durum, and most preferably the wheat is *Triticum aestivum* ssp. *aestivum*, herein also referred to as "breadwheat". As is understood in the art, hexaploid wheat such as bread wheat comprise three genomes which are commonly designated the A, B and D genomes, while tetraploid wheats such as durum wheat comprise two genomes commonly designated the A and B genomes. Each genome comprises 7 pairs of chromosomes which may be observed by cytological methods during meiosis and thus identified, as is well known in the art.

Wheat plant having grain with high β-glucan content: as used herein, refers to a wheat plant (*Triticum aestivumm*) which produces grain that has a β-glucan content of up to 2% β-glucan by dry weight of grain, wherein the high β-glucan trait is developed from traditional breeding and crossing and not transformation. Typically, a control or wild type wheat plant has a β-glucan expressed as a percentage w/w of grain dry weight, ranging from 0.18% to 0.89%. An exemplary "wheat plant having grain with high β-glucan content" is a plant from the lines 2015-627-41, 75; 2015-630-15 or 2015-23, or a wheat plant having a part of chromosome 7HL from a Betzes barley plant incorporated therein through traditional breeding, or a plant having a barley CslF6 gene from Betzes barley plant introgressed therein through traditional breeding, Using a High β-Glucan Wheat Cultivar to Develop Other Wheat Varieties.

Wheat varieties such as a high β-glucan wheat cultivar provide a source of breeding material that may be used to develop new wheat varieties. Plant breeding techniques known in the art and used in a wheat plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often, combinations of these techniques are used. The development of wheat varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.

Additional Breeding Methods

In an embodiment, this invention is directed to methods for producing a wheat plant by crossing a first parent wheat plant with a second parent wheat plant wherein either the first or second parent wheat plant is a high β-glucan wheat cultivar. The other parent may be any other wheat plant, such as a wheat plant that is part of a synthetic or natural population. Any such methods using a high β-glucan wheat cultivar are part of this invention: selfing, sibbing, backcrosses, mass selection, pedigree breeding, bulk selection, hybrid production, and crosses to populations. These methods are well known in the art and some of the more commonly used breeding methods are described below.

The following describes breeding methods that may be used with a high β-glucan wheat cultivar in the development of further wheat plants. One such embodiment is a method for developing a cultivar a high β-glucan wheat cultivar progeny wheat plant in a wheat plant breeding program comprising: obtaining the wheat plant, or a part thereof, of cultivar a high β-glucan wheat cultivar utilizing said plant or plant part as a source of breeding material and selecting a high β-glucan wheat cultivar progeny plant with molecular markers in common with cultivar a high β-glucan wheat cultivar and/or with morphological and/or physiological characteristics selected from the characteristics listed in the Tables herein. Breeding steps that may be used in the wheat plant breeding program include pedigree breeding, backcrossing, mutation breeding, and recurrent selection. In conjunction with these steps, techniques such as RFLP-enhanced selection, genetic marker enhanced selection (e.g., SSR markers) and the making of double haploids may be utilized.

Another method involves producing a population of a high β-glucan wheat cultivar progeny wheat plants, comprising crossing cultivar a high β-glucan wheat cultivar with another wheat plant, thereby producing a population of wheat plants, which, on average, derive 50% of their alleles from a high β-glucan wheat cultivar. A plant of this population may be selected and repeatedly selfed or sibbed with a wheat cultivar resulting from these successive filial generations. One embodiment of this invention is the wheat cultivar produced by this method and that has obtained at least 50% of its alleles from a high β-glucan wheat cultivar.

One of ordinary skill in the art of plant breeding would know how to evaluate the traits of two plant varieties to determine if there is no significant difference between the two traits expressed by those varieties. Thus, the invention includes a high β-glucan wheat cultivar progeny wheat plants comprising a combination of at least two cultivar a high β-glucan wheat cultivar traits selected from the group consisting of those listed in the Tables herein, so that said progeny wheat plant is not significantly different for said traits than a high β-glucan wheat cultivar. Using techniques described herein, molecular markers may be used to identify said progeny plant as a high β-glucan wheat cultivar progeny plant. Mean trait values may be used to determine whether trait differences are significant, and the traits may be measured on plants grown under the same environmental conditions. Once such a variety is developed its value is substantial, as it is important to advance the germplasm base as a whole in order to maintain or improve traits such as yield, disease resistance or tolerance, pest resistance or tolerance, and plant performance in extreme environmental conditions.

Progeny of a high β-glucan wheat cultivar may also be characterized through their filial relationship with a high β-glucan wheat cultivar, as for example, being within a certain number of breeding crosses of a high β-glucan wheat cultivar. A breeding cross is a cross made to introduce new genetics into the progeny, and is distinguished from a cross, such as a self or a sib cross, made to select among existing genetic alleles. The lower the number of breeding crosses in the pedigree, the closer the relationship between a high β-glucan wheat cultivar and its progeny. For example, progeny produced by the methods described herein may be within 1, 2, 3, 4 or 5 breeding crosses of a high β-glucan wheat cultivar.

Pedigree Breeding

Pedigree breeding starts with the crossing of two genotypes, such as a high β-glucan wheat cultivar and another wheat variety having one or more desirable characteristics that is lacking or which complements a high β-glucan wheat cultivar. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically, in the pedigree method of breeding, five or more successive filial generations of selfing and selection is practiced: F1 to F2; F2 to F3; F3 to F4; F4 to F5, etc. After a sufficient amount of inbreeding, successive filial generations will serve to increase seed of the developed variety. In an embodiment, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a wheat variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new wheat varieties.

Therefore, an embodiment of this invention is a method of making a backcross conversion of a high β-glucan wheat cultivar comprising the steps of crossing a plant of a high β-glucan wheat cultivar with a donor plant comprising a desired trait, selecting an F1 progeny plant comprising the desired trait, and backcrossing the selected F1 progeny plant to a plant of wheat cultivar a high β-glucan wheat cultivar. This method may further comprise the step of obtaining a molecular marker profile of a high β-glucan wheat cultivar and using the molecular marker profile to select for a progeny plant with the desired trait and the molecular marker profile of a high β-glucan wheat cultivar. In one embodiment, the desired trait is a mutant gene or transgene present in the donor parent.

Recurrent Selection and Mass Selection

Recurrent selection is a method used in a plant breeding program to improve a population of plants. A high β-glucan wheat cultivar is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation Breeding

Mutation breeding is another method of introducing new traits into wheat cultivars. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation, such as X-rays, Gamma rays (e.g. cobalt 60 or cesium 137), neutrons, (product of nuclear fission by uranium 235 in an atomic reactor), B radiation (emitted from radioisotopes such as phosphorus 32 or carbon 14), or ultraviolet radiation (optionally from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. In addition, mutations created in other wheat plants may be used to produce a backcross conversion of a high β-glucan wheat cultivar that comprises such mutation. Further embodiments of the invention are the treatment of a high β-glucan wheat cultivar with a mutagen and the plant produced by mutagenesis of a high β-glucan wheat cultivar.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing a high β-glucan wheat cultivar. Isozyme Electrophoresis and RFLPs have been widely used to determine genetic composition.

SSR technology is currently the most efficient and practical marker technology; more marker loci can be routinely used and more alleles per marker locus can be found using SSRs in comparison to RFLPs. Single Nucleotide Polymorphisms (SNPs) may also be used to identify the unique genetic composition of the invention and progeny varieties retaining that unique genetic composition. Various molecular marker techniques may be used in combination to enhance overall resolution. Wheat DNA molecular marker linkage maps have been rapidly constructed and widely implemented in genetic studies.

One use of molecular markers is QTL mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous genotype in the breeding program. For example, a wheat plant for which a high β-glucan wheat cultivar is a parent can be used to produce double haploid plants. Double haploids are produced by the doubling of a set of chromosomes (1N) from a heterozygous plant to produce a completely homozygous individual. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Methods for obtaining haploid plants have also been disclosed in the art.

Thus, an embodiment of this invention is a process for making a substantially homozygous a high β-glucan wheat cultivar progeny plant by producing or obtaining a seed from the cross of a high β-glucan wheat cultivar and another wheat plant and applying double haploid methods to the F1 seed or F1 plant, or to any successive filial generation. Based on studies in maize and currently being conducted in wheat, such methods would decrease the number of generations required to produce a variety with similar genetics or characteristics to a high β-glucan wheat cultivar.

In particular, a process of making seed retaining the molecular marker profile of a high β-glucan wheat cultivar is contemplated, such process comprising obtaining or producing F1 seed for which a high β-glucan wheat cultivar is a parent, inducing doubled haploids to create progeny without the occurrence of meiotic segregation, obtaining the molecular marker profile a high β-glucan wheat cultivar, and selecting progeny that retain the molecular marker profile of a high β-glucan wheat cultivar. Descriptions of other breeding methods that are commonly used for different traits and crops are known.

Further reproduction of the variety can occur by tissue culture and regeneration. Tissue culture of various tissues of wheat and regeneration of plants therefrom is well known and widely published. Thus, another aspect of this invention is to provide cells which upon growth and differentiation produce wheat plants having essentially all of the morphological and physiological characteristics of wheat cultivar a high β-glucan wheat cultivar. Means for preparing and maintaining plant tissue culture are well known in the art. By way of example, a tissue culture comprising organs has been used to produce regenerated plants.

Additional Trait Development Techniques

Recombinant DNA techniques may be used with the high to β-glucan wheat cultivar to develop further varieties and traits. In some embodiments of the invention, the invention is directed to a transgenic variant of the high to β-glucan wheat cultivars of the invention. A transgenic variant may contain at least one transgene but could contain at least 1, 2, 3, 4, 5, 6, 7, 8, 9, 10, or more transgenes. Another embodiment of the invention involves a process for producing high to β-glucan wheat cultivars further comprising a desired trait, said process comprising introducing a transgene that confers a desired trait to a wheat plant of the invention. Methods for producing transgenic plants have been developed and are well known in the art. As part of the invention, one of ordinary skill in the art may utilize any method of producing transgenic plants which is currently known or yet to be developed. Numerous methods for plant transformation have been developed, including biological and physical plant transformation protocols. In addition, expression vectors and in vitro culture methods for plant cell or tissue transformation and regeneration of plants are available. In certain embodiments, the desired trait may be one or more of herbicide tolerance or resistance, insect resistance or tolerance, disease resistance or tolerance, resistance for bacterial, viral, or fungal disease, male fertility, male sterility, decreased phytate, or modified fatty acid or carbohydrate metabolism. The specific transgene may be any known in the art or listed herein, including, but not limited to a polynucleotide conferring resistance to imidazolinone, dicamba, sulfonylurea, glyphosate, glufosinate, triazine, benzonitrile, cyclohexanedione, phenoxy propionic acid, and L-phosphinothricin; a polynucleotide encoding a *Bacillus thuringiensis* polypeptide, a polynucleotide encoding phytase, FAD-2, FAD-3, galactinol synthase or a raffinose synthetic enzyme, *Fusarium, Septoria*, or various viruses or bacteria. Various genetic elements can be introduced into the plant genome using transformation. These elements include, but are not limited to genes, coding sequences, inducible, constitutive, and tissue-specific promoters, enhancing sequences, and signal and targeting sequences.

In some embodiments, the recombinant genetic technique of gene editing may be used to create insertions or deletions to add additional traits or to modify the high β-glucan trait of the invention.

High β-Glucan Wheat Grain Products

Wheat may be used to produce a variety of products, including, but not limited to, grain, flour, baked goods, cereals, crackers, pasta, beverages, livestock feed, biofuel, straw, construction materials, and starches. The hard wheat classes are milled into flour used for breads, while the soft wheat classes are milled into flour used for pastries and crackers. Wheat starch is used in the food and paper industries as laundry starches, among other products.

The invention thus provides flour, meal or other products produced from the high β-glucan wheat grain. These may be unprocessed or processed, for example by fractionation or bleaching, or heat treated to stabilize the product such as flour. The invention includes methods of producing flour, meal, starch granules, starch or isolated β-glucan from the grain or from an intermediate product such as flour. Such methods include, for example, milling, grinding, rolling, flaking or cracking the grain. The invention also provides starch from grain of the exemplified wheat plants comprising increased amounts of dietary fiber, which may be measured by the methods described herein. In preferred embodiments, these products comprise an elevated level of β-glucan such as at least 2%.

The present invention also extends to wheat flour, such as wholemeal wheat flour, or other processed products obtained from the grain such as semolina, isolated wheat starch granules, isolated wheat starch or wheat bran produced from the grain of the invention. The (3-glucan content of the wholemeal flour is essentially the same as for the wheat grain, as described above. In an embodiment, the flour is wheat endosperm flour (white flour) comprising β-glucan wherein the β-glucan content of the flour is between 0.3% and about 3% (w/w). The white flour has a lower bran content than the wholemeal flour from which it is obtained. The flour or bran may have been stabilized by heat treatment.

The present invention also provides a food ingredient that comprises the grain, flour, isolated β-glucan or composition comprising β-glucan, or a drink ingredient comprising the isolated β-glucan or composition comprising β-glucan of the invention. It is preferred that the food or drink ingredient is packaged ready for sale. The food or drink ingredient may be incorporated into a mixture with another food or drink ingredient, such as, for example, a cake mix, a pancake mix or a dough. The food ingredient may be used in a food product at a level of at least 1%, preferably at least 10%, on a dry weight basis, and the drink ingredient may be used in a drink product at a level of at least 0.1% on a weight basis. If the food product is a breakfast cereal, bread, cake or other farinaceous product, higher incorporation rates are preferred, such as at a level of at least 20% or at least 30%. Up to 100% of the ingredient (grain, flour such as wholemeal flour etc.) in the food product may be an ingredient of the invention. Preferably, the food or drink product, when ready for consumption, comprises the β-glucan derived from the food or drink ingredient in essentially unaltered form.

The food or drink product of the invention may be used in altering one or more physiological parameters in an animal, preferably a human. The physiological parameter may be, for example, of metabolic health, bowel health or cardiovascular health, or of preventing or reducing the severity or incidence of metabolic, bowel or cardiovascular disease in an animal. The human may be a child or an adult human, male or female. Alternatively, the animal may be a livestock animal such as pigs, cattle or sheep, a pet animal such as dogs or cats, or farmed animals such as fish, poultry such as chickens, ducks or turkeys.

The grain of the present invention and the ingredients obtained therefrom may be blended with essentially wild-type grain or other ingredients. The invention therefore provides a composition comprising traditional wheat grain or an ingredient obtained therefrom, the traditional wheat grain having a level of β-glucan of less than 2% (w/w), in addition to the wheat grain of the invention or an ingredient obtained therefrom. In such compositions, it is preferred that the grain of the present invention and/or the ingredient obtained therefrom comprises at least 10% by weight of the composition. The traditional wheat grain ingredient may be, for example, flour such as wholemeal flour, semolina, a starch-containing ingredient, purified starch or bran.

The grain of the present invention may also be milled to produce a milled wheat product. This will typically involve obtaining wheat grain, milling the grain to produce flour, and optionally, separating any bran from the flour. Milling the grain may be by dry milling or wet milling. The grain may be conditioned to having a desirable moisture content prior to milling, preferably about 10% or about 14% on a weight basis, or the milled product such as flour or bran may be processed by treatment with heat to stabilize the milled product. As will be understood, the β-glucan content of the milled product corresponds to the β-glucan content in the wheat grain or the component of the wheat grain which is represented in the milled product. β-glucan, a composition comprising β-glucan, starch granules or starch may also be extracted from the grain of the present invention to produce β-glucan, starch granules or starch, and the invention therefore provides a method of producing these. The extraction process typically comprises obtaining a milled product from the grain, and may comprise a water-soluble extraction of the milled product, which extraction may be under neutral (pH about 6-8) or alkaline conditions. The starch may be characterized by one or more properties as described for the starch in the grain of the invention. The β-glucan, starch granules or starch produced by the method are preferably at least 60% pure, more preferably at least 90% pure on a dry weight basis.

The present invention also provides a method of producing a product comprising β-glucan, wherein the method comprises (i) obtaining or producing a wheat grain of the present invention, or flour therefrom, and (ii) processing the wheat grain or flour therefrom to produce the product. This method may further comprise a step of assessing the level or type of β-glucan in the wheat grain or flour of step (i) or in the product of step (ii), or a step of adding a processed wheat grain or flour from step (ii) to another food or drink ingredient, thereby producing the product comprising β-glucan. The product may be a food or drink product or a pharmaceutical composition, or isolated β-glucan. Preferred food products include bread, breakfast cereals, biscuits, muffins, muesli bars, noodles.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, chapatti, roti, nan, animal food or pet food.

The present invention also provides a use of the β-glucan compositions isolated from wheat grain of the invention, which may be used as a low calorie food additive, a bulking agent, a dietary fiber, a texturizing agent, a preservative, a probiotic agent or any combination of these uses. Preferably, these uses are embodied in food products of the invention, by incorporating the β-glucan in the food product. The present invention therefore also provides a product, preferably a food product, which comprises the β-glucan which has been incorporated for the aforesaid use.

The present invention also provides a method of altering one or more physiological parameters in an animal, or of preventing or reducing the severity or incidence of a disease, the method comprising providing to the animal the grain of the present invention, or a food or drink product made therefrom, wherein the altered physiological parameter or reduced severity or incidence of disease is relative to providing to the animal the same amount of a corresponding wild-type grain or food or drink product made therefrom. It is preferred that the physiological parameter is a parameter of metabolic health, bowel health or cardiovascular health, such as a reduced incidence or severity of diabetes, bowel disease, obesity, hypertension, constipation, osteoporosis, cancer or cardiovascular disease. The physiological parameter may be one or more of: an increased number of beneficial intestinal bacteria, a reduced number of aberrant crypt foci in the bowel, an increased mineral absorption from the bowel, a reduced level of insulin in the blood, a reduced glycaemic index response, a reduced glycaemic load response, a reduced blood glucose level, a reduced blood pressure, a reduced body weight, a reduced blood cholesterol level or LDL cholesterol level, increased blood HDL cholesterol level, an increased bone density, or more frequent bowel movement.

It is preferred that the animal is a human, and the amount of grain, or food or drink produced therefrom, provided to the human is at least 10 g per day of the grain or grain equivalent.

Measuring β-Glucan Content

In general, β-glucan content is measured using any method known in the art. In some exemplary embodiments, β-glucan is determined using e.g., AACC International Approved Method 32-23; a Megazyme mixed-linkage β-glucan assay kit (Megazyme International Ireland Ltd., Bray Business Park, Bray, Co. Wicklow, Ireland), etc. In one exemplary embodiment, β-glucan content is measured according to the method of Hu and Barton 2008 (Gongshe Hu and Charlotte Burton (2008) Cereal Chemistry 85: 648-653, which is incorporated herein by reference).

Examples

Development of complete set of wheat-barley group-7 Robertsonian translocation chromosomes conferring increased content of β-glucan Materials and Methods Plant Material The material used in this study included barley (*Hordeum vulgare* L.) cv. 'Betzes' (TA9001), wheat (*Triticum aestivum* L.) cv 'Chinese Spring' (CS); wheat CS—barley Betzes 7H chromosome addition line (TA3697) from a set of lines produced by (Islam et al. 1978); wheat CS—barley Betzes 7HS and 7HL ditelosomic addition lines (TA3588 and TA3587) (Islam et al. 1981); and CS wheat monosomic stocks CSM7A, CSM7B, CSM7D (TA3047, TA3054 and TA3061 respectively). All lines are maintained at the Wheat Genetic Resources Center at Kansas State University.

Cytogenetic Analyses

The genomic in situ hybridization (GISH) was performed according to protocols from (Zhang et al. 2001) with modifications described by Danilova et al. (2016). The GISH probe mixture (20 μl/slide) contained 40 ng of barley gDNA probe labeled with fluorescein-12-dUTP (PerkinElmer, Waltham, Mass., USA cat. #NEL413001EA), 1 ng of Cy5-(GAA)9 oligonucleotide probe (synthesized by Integrated DNA Technologies, Inc., Coralville, Iowa, USA) and no wheat blocking DNA.

Fluorescent in situ hybridization (FISH) with oligonucleotide probes labeling repeats FAM-pAs1 and FAM-(GAA)9, cDNA probe 7S-4 (tp1b0015e09) physically mapped to the short arm of group-7 wheat chromosomes (Danilova et al. 2014) was used to determine the structure of translocation chromosomes. Physical position of the CslF6 gene and cDNA sequences used for KASP marker development were verified by FISH. Chromosome preparations, probe labeling, and the FISH procedure were as described previously (Kato et al. 2006; Kato et al. 2004) with minor modifications (Danilova et al. 2012). Wheat full length cDNA clones were obtained from the National BioResource Project-Wheat, Yokohama, Japan. Barley full length cDNA clones AK353650 and AK365097 were obtained from the Genebank of the National Institute of Agrobiological Sciences, Tsukuba, Japan. The average relative distance of a cDNA FISH site from the centromere was measured and calculated on 5 chromosomes using the MicroMeasure 3.3 software (Reeves and Tear 2000).

To paint barley chromosomes using FISH, a probe to barley specific copia-like retroelement BARE-1 (Manninen and Schulman 1993; Waugh et al. 1997; Wicker et al. 2009) was developed using sequence Z17327 and BARE LTR primers (Table 1).

Images were captured using a Zeiss Axioplan 2 microscope with a cooled charge-coupled device camera CoolSNAP HQ2 (Photometrics, Tucson, Ariz., USA) and AxioVision 4.8 software (Carl Zeiss, Thornwood, N.Y., USA). Images were processed using the Adobe Photoshop software (Adobe Systems Incorporated, San Jose, Calif., USA).

Molecular Markers Analysis

Genomic DNA was isolated from leaves of 3-week-old seedlings using a BioSprint 96 workstation according to the Qiagen BioSprint DNA Plant Handbook protocol (Cat. No. 941558, QIAGEN Inc., Valencia, Calif., USA).

Genotyping was conducted using an 8 μl Kompetitive Allele Specific PCR (KASP) reaction mixture containing 4 μl of DNA sample with a concentration of 10-20 ng/μl, 0.11 μl of 72× primer mix, and 4 μl of a 2×KASP master mix (LGC Genomics, Beverly, Mass., USA). The KASP PCR was run at PTC-221 MJ Research thermal cycler under following conditions: primer pair 5—initial denaturation at 94° C. for −15 min and 45 cycles of 94° C. for 20 sec, 56° C. for 1 min; primer pair 10—initial denaturation at 94° C. for −15 min, then 10 cycles 94° C. for 20 sec, 63° C. (drop 0.6° C. every cycle) for 1 min followed by 43 cycles of 94° C. for 20 sec, 56° C. for 1 min. The PCR results were read at BioRad CFX96 machine (BioRad Laboratories, Inc., Hercules, Calif., USA), after reading cycle: 37° C. for 1 min, with Bio-Rad CFX Manager 3.1 software. KASP PCR primer sequences are listed in Table 1. Primers were synthesized by Integrated DNA Technologies, Inc., Coralville, Iowa, USA.

Compensation Test and β-Glucan Content

The ability of barley chromosome arms 7HS and 7HL to compensate for a homologous part of wheat genome was tested on plants that were homozygous for the translocation chromosomes. The fertility was estimated by average amount of seeds per spikelet, calculated for 3 heads harvested from 5 plants, grown in a greenhouse. Average was calculated for 5 plants, confidence intervals were calculated for confidence level equal 95%.

B-glucan content in grain, % per dry weight was measured by Medallion Labs (General Mills Inc., Minneapolis, Minn.) in two replicates.

Results

Physical Mapping of CslF6 Gene and Barley cDNA

Figure 1:
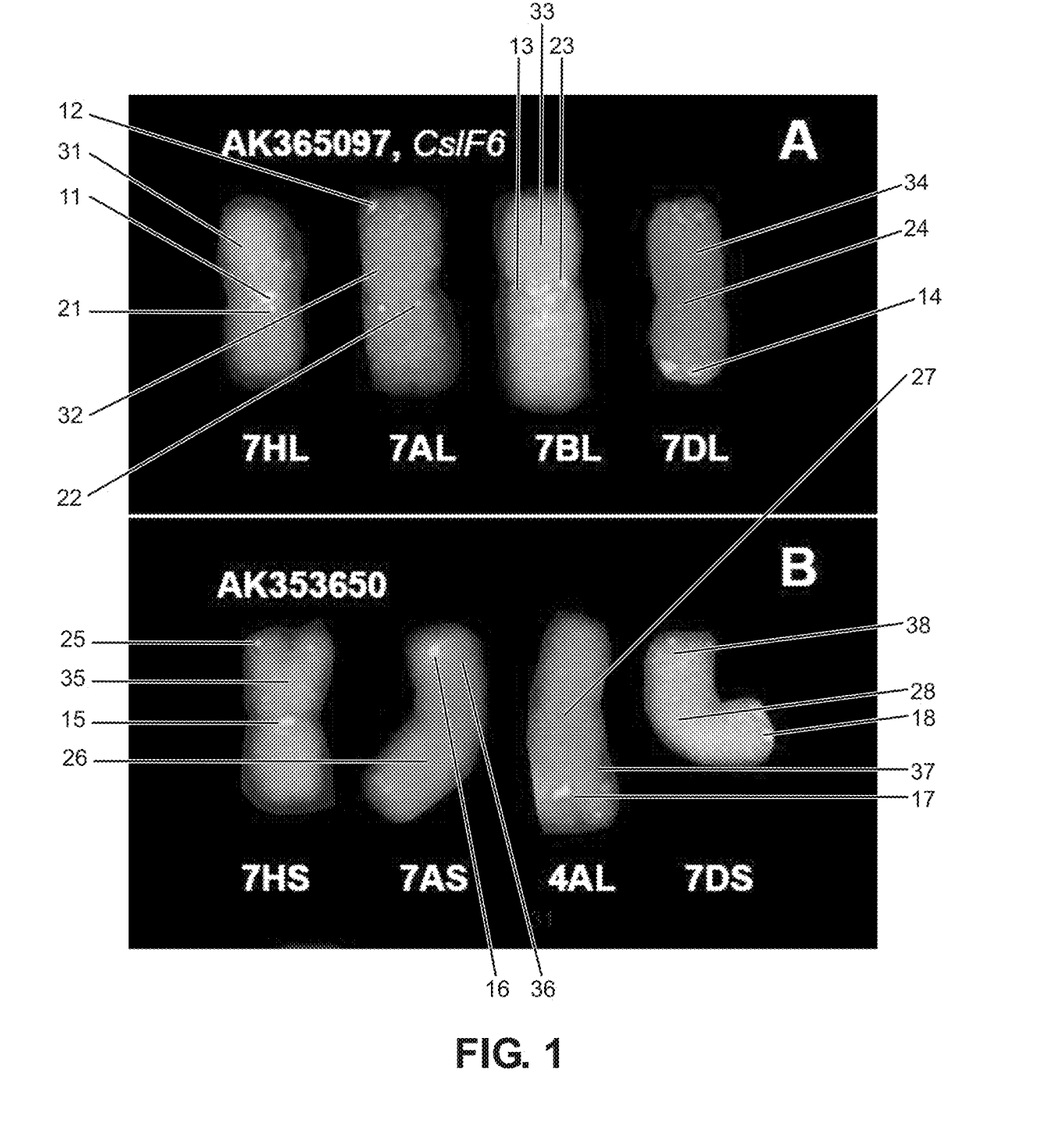

The Cslf6 cDNA FISH probe was hybridized to wheat—barley chromosome 7H addition line and signals were detected near the centromere (relative distance 0.1) on the long arms of all group 7 wheat and barley chromosomes (FIG. 1A). This result is in agreement with BLAST search (Altschul et al. 1990) against the CS wheat flow-sorted chromosome sequence database (Mayer et al. 2014): sequences with approximately 95% nucleotide identity to barley Cslf6 cDNA were found in 7L arms of all three wheat genomes.

FISH was used to verify the physical position of cDNA sequence selected for molecular marker development. Barley cDNA probe AK353650 was detected on the distal ends of chromosome arms 7HS, 7AS, 7DS and 4AL at relative distance 0.9 (FIG. 1B). The presence of this probe on the long arm of chromosome 4A is caused by a species-specific cyclic translocation involving chromosomes 4A, 5A, and 7B, which is present in all accessions of T. turgidum L. and T. aestivum.

Development of 7H Specific KASP Markers

Figure 2:
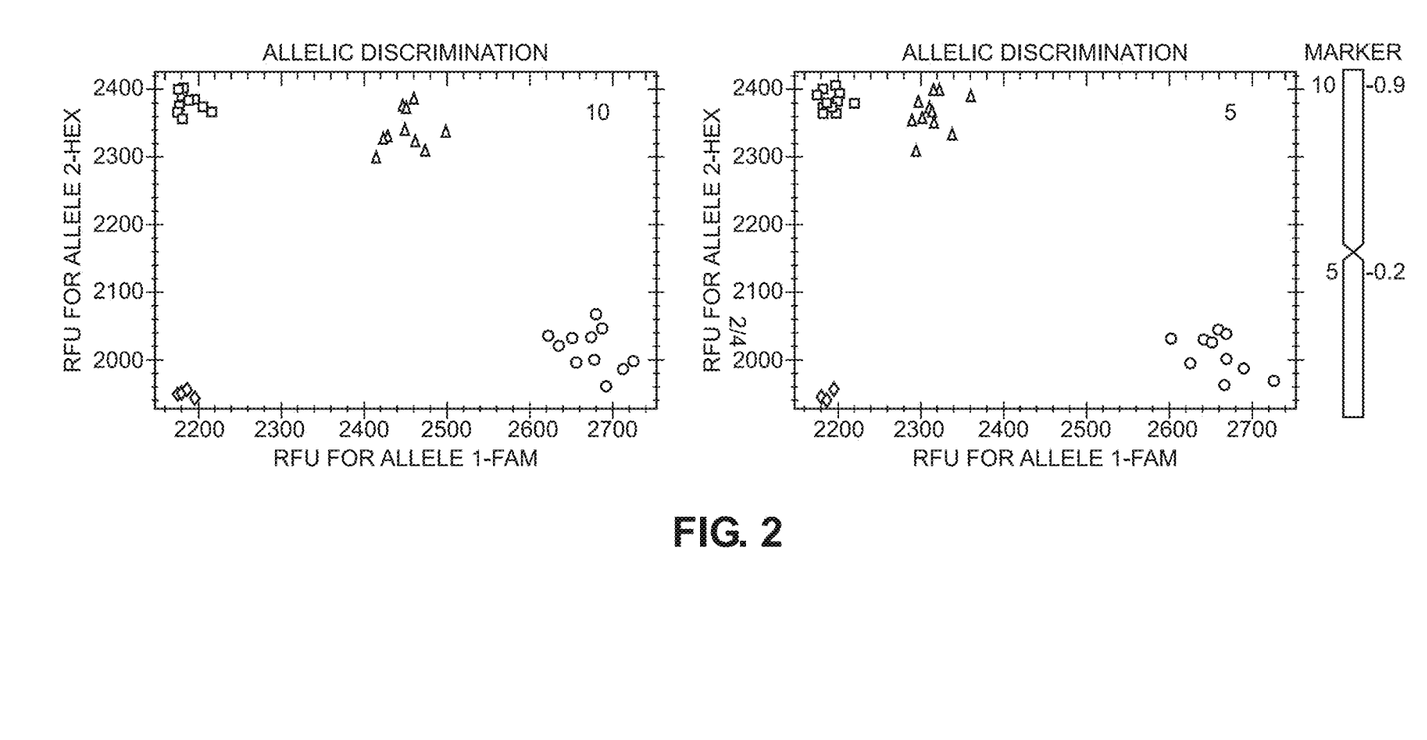

Kompetitive Allele Specific PCR (KASP) markers (LGC Genomics, Beverly, Mass., USA) with determined physical positions were developed for barley and wheat chromosome arms 7S and 7L using sequences of physically mapped wheat cDNA tp1b0013b07 •7L near the centromere (fraction length (FL) 0.2) and barley cDNA AK353650 •7HS close to the telomere (FL 0.9) (Danilova et al. 2014). The position of barley sequence was detected on the barley physical map of chromosome 7H and verified by FISH as described above. Barley sequences of cv 'Morex', 'Barke' and 'Bowman' (Mayer et al. 2012) were compared with the corresponding wheat A-, B-, and D-genome sequences from flow sorted wheat CS sequences database (Mayer et al. 2014) to reveal single nucleotide polymorphism (SNP) and develop KASP primers. The KASP assays correctly discriminated between barley cv 'Betzes'; plants heterozygous for wheat and barley alleles (ditelosomic addition lines TA3588 for 7HS marker 10 and TA3587 for 7HL marker 5), and wheat CS (FIG. 2) and were used for further screenings.

Development of Wheat-Barley Translocation Lines

The monosomic stocks CSM7A, CSM7B and CSM7D were crossed with the 7H addition line TA3697 and three sets of double monosomic lines were selected from the F1 progenies by chromosome count. The progenies of plants from three double monosomic populations were screened with KASP markers and plants with disassociation of barley 7HS and 7HL markers were analyzed by GISH. In total 1281 seedlings from 3 populations were screened (Table 2). The number of seedlings without barley chromosome (both 7HS and 7HL molecular markers were negative) and with complete barley chromosome (both 7HS and 7HL molecular markers were positive) were similar in three populations at 40-45% each. The remaining 15-20% of seedlings had broken barley chromosome represented by telosomes, isochromosomes, Robertsonain Translocations (RobTs), and dicentric chromosomes (Table 2). These data demonstrate that in 80-85% of pollen mother cells of double monosomic plants wheat and barley group 7 chromosomes segregate normally and in at least 15-20% cells barley chromosomes were broken at centromeres. Most of the broken 7H chromosomes were stabilized as telosomes and only 2-3% fused and formed RobTs or structures with two centromeres—dicentric chromosomes. The frequency of group-7 compensating translocation chromosomes was 0.3-0.9%.

Figure 3:
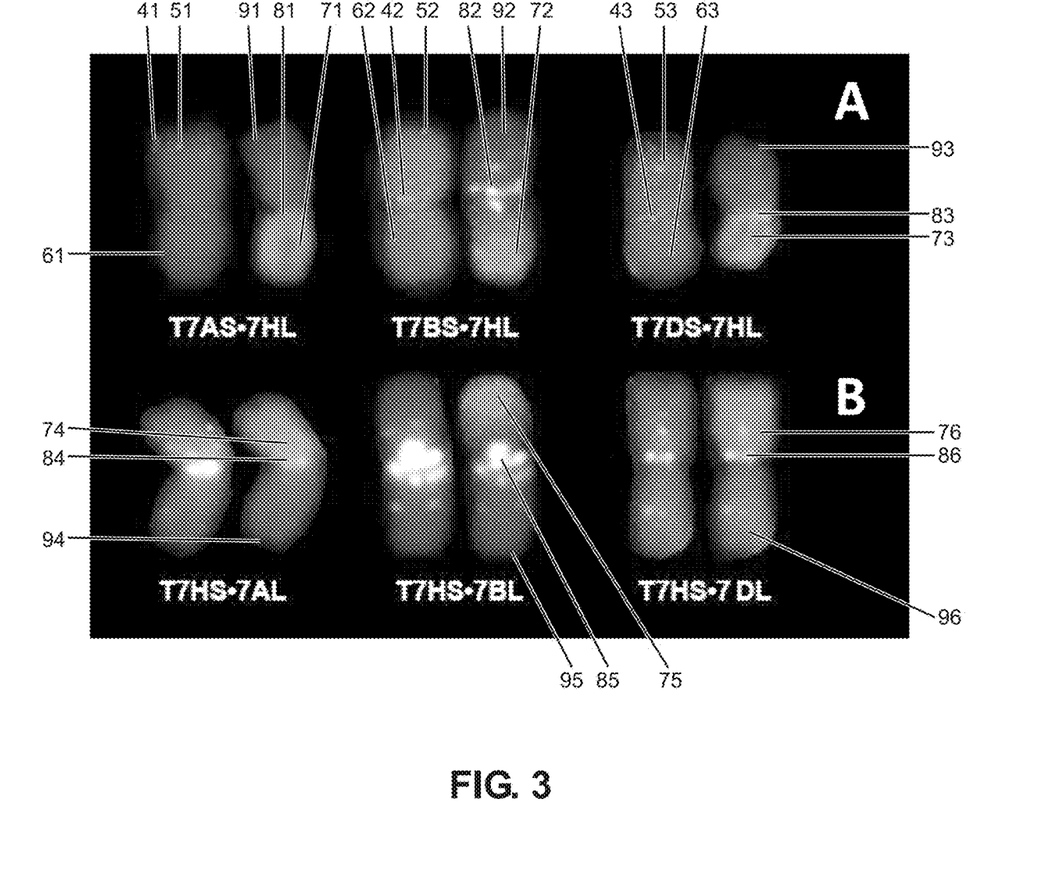
Figure 4:
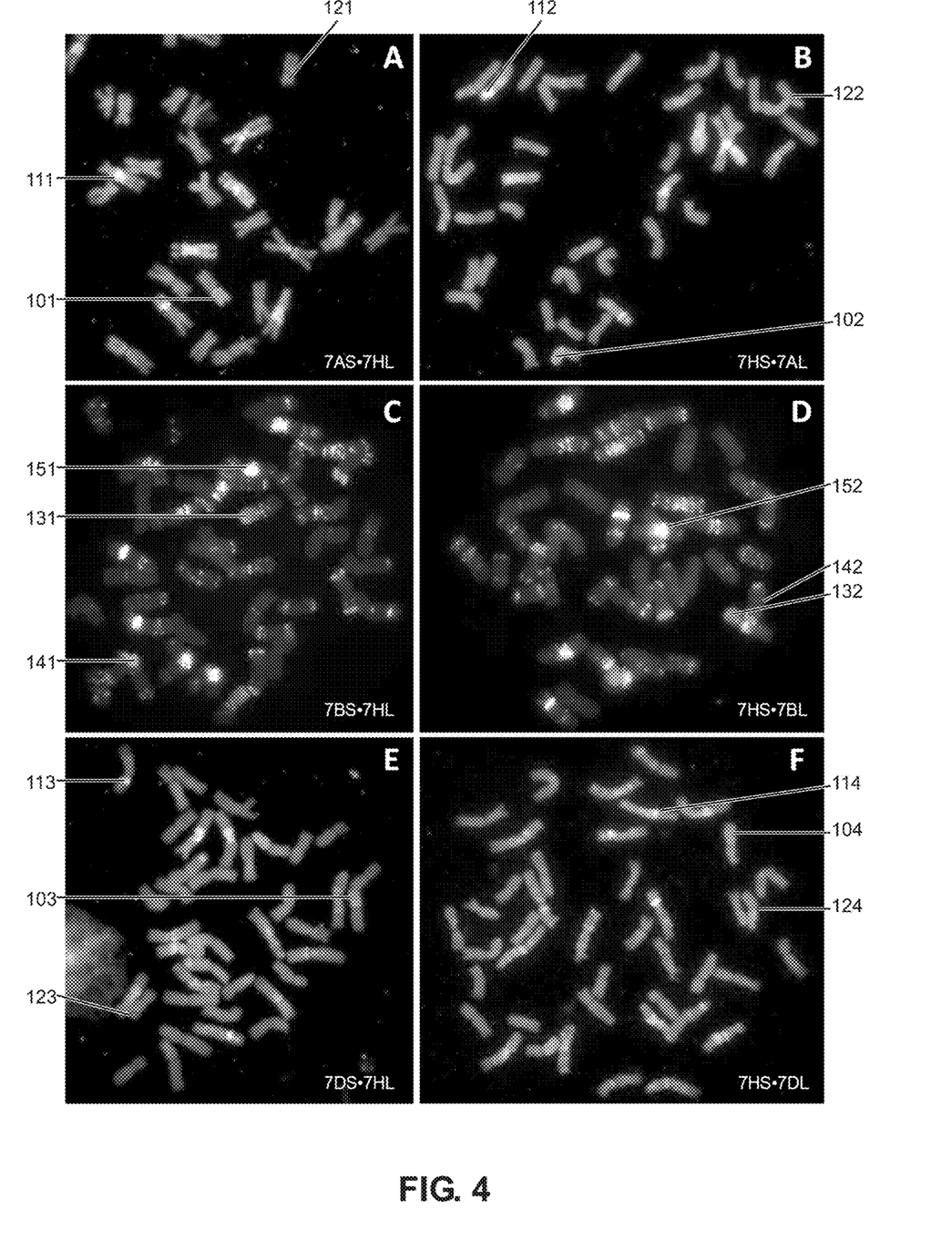

To verify the structure of the translocation chromosomes, we combined molecular marker and cytogenetic analyses. The barley 7HS and 7HL chromosomal arms were identified by KASP markers and confirmed cytologycally by $(GAA)_n$-banding to distinguish the short arm of barley chromosome 7H which has a distinctive interstitial $(GAA)_n$ site (FIG. 1, 3). FISH with cDNA tp1b0015e09 probe 7S-4 physically mapped on chromosome arms 7S and pAs1- and $(GAA)_n$-painting enabled identification of wheat chromosomal arms involved in these translocations (FIG. 3). The wheat CS chromosomal arm 7AL has a much weaker $(GAA)_n$ signals located more proximal than the $(GAA)_n$ signals on 7AS. The wheat 7DL arm has a distinctive interstitial $(GAA)_n$ band, that is absent in 7DS (FIG. 1). The wheat 7BL arm was also identified by its specific $(GAA)_n$ pattern. Compensating RobTs involving all six wheat group-7 chromosome arms and barley 7H arms were recovered (Table 2, FIG. 3). Independent breakage-fusion events resulted in two T7HS•7BL, two T7HS•7DL and three T7DS•7HL RobTs. Plants with RobTs were self-pollinated and homozygous progenies were selected by KASP markers and confirmed by GISH (FIG. 4). These plants were used for further analysis. These homozygous translocation lines were given accession numbers and are held in the Wheat Genetics Resource Center, Kans. State University, Manhattan, Kans. (Table 3)

Characterization of Wheat-Barley Translocation Lines.

To determine the ability of barley chromosome arms 7HS and 7HL to compensate for the loss of homoeologous wheat arms, sporophytic compensation was determined as seed set per spikelet. The fertility of all homozygous translocation lines did not differ significantly from the CS wheat control (Table 4). It was observed that most plants with RobTs involved 7HS were more vigorous, had longer spikes and higher grain yield per plant then plants with 7HL (Table 4).

The β-glucan content in grain, harvested from plants, homozygous on wheat-barley translocation chromosomes involved barley chromosome arm 7HL was 1.4-1.8 times higher than in the CS wheat control and RobT involving chromosome arm 7HS (Table 5).

TABLE 1

PCR and KASP primers

| Marker | Forward primer | Reverse primer | PCR product, bp | Sequence | Position on chromosome |
|---|---|---|---|---|---|
| 10 | TGCAGAACTAGCACAAGTATCCATAG (SEQ ID NO: 1) TGCAGAACTAGCACAAGTATCCACT (SEQ ID NO: 2) | GATGTGGGGAGTTGATGATGAC (SEQ ID NO: 7) | 106 | AK353650 | 7HS 0.9 |
| 5 | TCAGATTCTAAGAGTATTGGATTCTGGA (SEQ ID NO: 3) TCAGATTCTAAGAGTATTGGCTTCCGGG (SEQ ID NO: 4) | CCTGGAAGCTGAATCGAATTTAC (SEQ ID NO: 8) | 69 | tplb0013b07 | 7WL 0.2 |
| BARE LTR5 | GGGAGTGACGAATGGGTT (SEQ ID NO: 5) | AGCAAGAGAGACGGAAAGGTAGA (SEQ ID NO: 9) | | Z17327 | |
| BARE LTR3 | GCCCCTGCGCAGGATAAGAGA (SEQ ID NO: 6) | CGATCTAGTGCCGAACGGACGAC (SEQ ID NO: 10) | | Z17327 | |

TABLE 2

Screening of double monosomic progenies

| Barley chromatin constitution | F₂ CSM7A × DA7H total | % | F₂ CSM7B × DA7H total | % | F₂ CSM7D × DA7H Total | % |
|---|---|---|---|---|---|---|
| Telosome 7HS | 8 | 2.0 | 13 | 6.0 | 43 | 6.4 |
| Telosome 7HL | 32 | 8.1 | 9 | 4.2 | 38 | 5.7 |
| Whole 7H* | 156 | 39.7 | 88 | 40.7 | 252 | 37.5 |
| Isochromosome 7HS•7HS | 3 | 0.8 | 2 | 0.9 | 10 | 1.5 |
| Isochromosome 7HL•7HL | 16 | 4.1 | 2 | 0.9 | 28 | 4.2 |
| Translocation 7AS•7HL | 2 | 0.5 | 0 | 0 | 0 | 0 |
| Translocation 7HS•7AL | 1 | 0.3 | 0 | 0 | 0 | 0 |
| Translocation 7DS•7HL | 0 | 0 | 0 | 0 | 2 | 0.3 |
| Translocation 7HS•7DL | 0 | 0 | 0 | 0 | 3 | 0.4 |
| Translocation 7BS•7HL | 0 | 0 | 1 | 0.5 | 0 | 0 |
| Translocation 7HS•7BL | 0 | 0 | 2 | 0.9 | 0 | 0 |
| Translocation ?W•7HL | 4 | 1.0 | 2 | 0.9 | 3 | 0.4 |
| Translocation 7HS•?W | 1 | 0.3 | 0 | 0 | 5 | 0.7 |
| Dicentric chromosome W•7HS | 1 | 0.3 | 1 | 0.5 | 0 | 0 |
| Dicentric chromosome W•7HL | 1 | 0.3 | 1 | 0.5 | 2 | 0.3 |
| Mini barley chromosome** | 0 | 0 | 0 | 0 | 4 | 0.6 |
| No barley chromosome** | 168 | 42.6 | 95 | 44.0 | 282 | 42 |
| Total plants screened | 393 | | 216 | | 672 | |

*not checked by GISH
**detected by GISH only in plants with marker disassociation. Not scored in other plants

TABLE 3

Wheat Genetics Resource Center accession numbers for wheat-barley Robertsonian translocation (RobT) lines

| Translocation | Accession Number |
|---|---|
| 7AS•7HL | TA5790 (exp number 2015-627-41, 75) |
| 7HS•7AL | TA5791 (exp number 2015-541-13, 27) |
| 7BS•7HL | TA5792 |
| 7HS•7BL | TA5793 |
| 7DS•7HL | TA5795-L1 (exp number 2015-630-15) TA5795-L2 (exp number 2015-629-23) |
| 7HS•7DL | TA5796-L1 TA5796-L2 TA5796-L3 |

TABLE 4

Spikelet fertility compensation test for wheat - barley translocation lines.

| # | RobT | Accession | Average number of kernels per spikelet P = 0.05 | Average grain mass per plant, g |
|---|---|---|---|---|
| 1 | 7HS•7AL | 2016-480 | 2.69 ± 0.33 | 14.7 |
| 2 | 7HS•7BL | 2016-466-05, 16 | 2.15 ± 0.22 | 12.1 |
| 3 | 7HS•7DL | 2019-479 | 2.42 ± 0.29 | 12.1 |
| 4 | 7HS•7DL | 2016-484 | 2.26 ± 0.42 | 9.9 |
| 5 | 7AS•7HL | 2016-481 | 2.14 ± 0.12 | 9.1 |
| 6 | 7BS•7HL | 2016-486 | 1.93 ± 0.19 | 11.6 |
| 7 | 7DS•7HL | 2016-482 | 2.39 ± 0.31 | 10.1 |
| 8 | 7DS•7HL | 2016-483 | 2.46 ± 0.16 | 12.8 |
| 9 | 7DS•7HL | 2016-485 | 2.21 ± 0.34 | 10.5 |
| 10 | control | CS | 2.42 ± 0.19 | 15.13 |

TABLE 5

β-glucan content of wheat - barley translocation lines.

| Genotype | β-glucan, % |
|---|---|
| Wheat cv Chinese Spring | 0.89 |
| 2015-627-41, 75 (7AS•7HL) | 1.23 |
| 2015-541-13, 27 (7HS•7AL) | 0.92 |
| 2015-630-15 (7DS•7HL) | 1.31 |
| 2015-629-23 (7DS•7HL) | 1.57 |

REFERENCES

Altschul, S. F., W. Gish, W. Miller, E. W. Myers and D. J. Lipman, 1990 Basic Local Alignment Search Tool. Journal of Molecular Biology 215: 403-410.

Danilova, T. V., B. Friebe and B. S. Gill, 2012 Single-copy gene fluorescence in situ hybridization and genome analysis: Acc-2 loci mark evolutionary chromosomal rearrangements in wheat. Chromosoma 121: 597-611.

Danilova, T. V., B. Friebe and B. S. Gill, 2014 Development of a wheat single gene FISH map for analyzing homoeologous relationship and chromosomal rearrangements within the Triticeae. Theoretical and Applied Genetics 127: 715-730.

Islam, A. K. M. R., K. W. Shepherd and D. H. B. Sparrow, 1978 Production and characterization of wheat-barley addition lines. Proc. 5th Int. Wheat Genet. Symp. (New Delhi) 365-371.

Islam, A. K. M. R., K. W. Shepherd and D. H. B. Sparrow, 1981 Isolation and Characterization of Euplasmic Wheat-Barley Chromosome Addition Lines. Heredity 46: 161-&.

Kato, A., P. S. Albert, J. M. Vega and J. A. Birchler, 2006 Sensitive fluorescence in situ hybridization signal detection in maize using directly labeled probes produced by high concentration DNA polymerase nick translation. Biotech Histochem 81: 71-78.

Kato, A., J. C. Lamb and J. A. Birchler, 2004 Chromosome painting using repetitive DNA sequences as probes for somatic chromosome identification in maize. Proceedings of the National Academy of Sciences of the United States of America 101: 13554-13559.

Manninen, I., and A. H. Schulman, 1993 Bare-1, a Copia-Like Retroelement in Barley (*Hordeum vulgare* L). Plant Molecular Biology 22: 829-846.

Mayer, K. F. X., J. Rogers, J. Dolezel, C. Pozniak, and K. Eversole et al., 2014 A chromosome-based draft sequence of the hexaploid bread wheat (*Triticum aestivum*) genome. Science 345.

Mayer, K. F. X., R. Waugh, P. Langridge, T. J. Close, and R. P. Wise et al., 2012 A physical, genetic and functional sequence assembly of the barley genome. Nature 491: 711-717.

Reeves, A., and J. Tear, 2000 MicroMeasure for Windows, version 3.3, pp.

Waugh, R., K. Mclean, A. J. Flavell, S. R. Pearce, and A. Kumar et al., 1997 Genetic distribution of Bare-1-like retrotransposable elements in the barley genome revealed by sequence-specific amplification polymorphisms (S-SAP). Molecular & General Genetics 253: 687-694.

Wicker, T., S. Taudien, A. Houben, B. Keller, and A. Graner et al., 2009 A whole-genome snapshot of 454 sequences exposes the composition of the barley genome and provides evidence for parallel evolution of genome size in wheat and barley. Plant Journal 59: 712-722.

Zhang, P., B. Friebe, A. J. Lukaszewski and B. S. Gill, 2001 The centromere structure in Robertsonian wheat-rye translocation chromosomes indicates that centric breakage-fusion can occur at different positions within the primary constriction. Chromosoma 110: 335-344.

DEPOSIT STATEMENT

A deposit of seed of wheat cultivars TA5790, TA5792, and TA5795 disclosed herein, is and has been maintained by Wheat Genetic Resources Center at Kansas State Throckmorton Plant Sciences Center, Department of Plant Pathology Manhattan, Kans. 66506-5502 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will make available to the public without restriction a deposit of at least 2500 seeds of each variety or line with the American Type Culture Collection (ATCC), Rockville, Md., 20852. The seeds deposited with the ATCC have been taken from the same deposit maintained at Wheat Genetic Resources Center at Kansas State University as described above. On 5 Feb. 2018, wheat cultivar TA5790 was deposited with ATCC designation PTA-124874; wheat cultivar TA5792 was deposited with ATCC designation PTA-124875; and wheat cultivar TA5795 was deposited with ATCC designation PTA-124876. Additionally, Applicant(s) will meet all the requirements of 37 C.F.R. § 1.801-1.809, including providing an indication of the viability of the sample.

This deposit of the aforementioned wheat varieties will be maintained in the ATCC Depository, which is a public depository, for a period of 30 years, or 5 years after the most recent request, or for the enforceable life of the patent, whichever is longer, and will be replaced if it ever becomes nonviable during that period. Applicant will impose no restrictions on the availability of the deposited material from the ATCC; however, Applicant has no authority to waive any restrictions imposed by law on the transfer of biological material or its transportation in commerce.

What is claimed is:

1. A wheat plant, or a part thereof, produced by growing a seed of wheat line TA5790, representative seed of such line having been deposited with the American Type Culture and having been assigned ATCC Patent Deposit Designation PTA-124874.

2. A method of producing a wheat seed comprising crossing two wheat plants and harvesting the resultant wheat seed, wherein at least one wheat plant is the wheat plant of claim 1.

3. A wheat seed produced by the method of claim 2, wherein the seed comprises all morphological and physiological characteristics of wheat line TA5790.

4. A wheat plant, or a part thereof, produced by growing the seed of claim 3.

5. The wheat plant of claim 1, wherein the wheat plant has grain with high β-glucan content.

6. A plant part of the plant of claim 1, wherein the plant part comprises at least one cell of said plant.

7. The plant part of claim 6, further defined as head, awn, leaf, pollen, ovule, embryo, cotyledon, hypocotyl, meristematic cell, root, root tip, pistil, anther, floret, seed, pericarp, spike, stem, and callus.

8. The grain from the wheat plant of claim 4.

* * * * *